United States Patent [19]

Kato

[11] Patent Number: 5,854,079
[45] Date of Patent: Dec. 29, 1998

[54] METHOD FOR DETECTION OF PERFORMANCE REDUCTION OF EXHAUST GAS PURIFICATION CATALYST

[75] Inventor: Nobuhide Kato, Ama-gun, Japan

[73] Assignee: NGK Insulators, Ltd., Japan

[21] Appl. No.: 760,402

[22] Filed: Dec. 4, 1996

[30] Foreign Application Priority Data

Dec. 15, 1995 [JP] Japan .................................. 7-326959

[51] Int. Cl.$^6$ ........................... G01N 27/00; B01J 8/02
[52] U.S. Cl. .......................... 436/152; 436/147; 436/155; 423/212; 423/213.2; 423/224; 423/235; 423/239.1; 423/DIG. 6; 423/DIG. 13; 60/272; 60/273; 60/282; 60/299; 502/514; 502/515
[58] Field of Search ............................... 423/212, 213.2, 423/224, 235, 239.1, DIG. 6, DIG. 13; 60/272, 273, 282, 299; 502/55, 514, 515; 436/147, 152, 185

[56] References Cited

U.S. PATENT DOCUMENTS 5,613,360   3/1997   Iwai et al. .................................. 60/284

FOREIGN PATENT DOCUMENTS

| 442468 | 8/1991 | European Pat. Off. . |
| 3710268 | 10/1988 | Germany . |
| 62-61919 | 4/1987 | Japan . |
| 63-83415 | 6/1988 | Japan . |
| 91/14855 | 10/1991 | WIPO . |

*Primary Examiner*—Ponnathapura Achutamurthy
*Attorney, Agent, or Firm*—Parkhurst & Wendel, L.L.P

[57] ABSTRACT

A method for detection of the performance reduction of an exhaust gas purification catalyst used for reducing the concentration(s) of combustible components or (and) nitrogen oxides all present in an exhaust gas, which method detects a reduction in the heat amount $E_g$ generated from the exhaust gas by the reaction of the exhaust gas catalyzed by the catalyst, or a reduction in the cumulative heat amount generated from the exhaust gas by said reaction in a predetermined temperature range taken by the catalyst during its temperature increase. This method can detect the performance reduction of the catalyst accurately without conducting constant-speed vehicle running for a long time.

11 Claims, 5 Drawing Sheets

METHOD FOR DETECTION OF PERFORMANCE REDUCTION OF EXHAUST GAS PURIFICATION CATALYST

BACKGROUND OF THE INVENTION

1. Field of the Invention

The present invention relates to a method for detection of the performance reduction of an exhaust gas purification catalyst used in an automobile or the like.

2. Description of Related Art

Exhaust gases are discharged from, for example, internal combustion engines, external combustion engines and combustion furnaces all using, as the fuel, a heavy oil, a gas oil, a gasoline, a natural gas or the like, and contain unburnt combustible components (e.g. hydrocarbons, carbon monoxide and hydrogen), nitrogen oxides, etc. In order to oxidize the combustible components and reduce the nitrogen oxides to reduce their contents in exhaust gas, exhaust gas purification catalysts are in wide use in automobile engines, etc. Generally known as the exhaust gas purification catalysts are those catalysts containing a noble metal(s) such as platinum, palladium, rhodium or (and) the like.

These exhaust gas purification catalysts, when used for a long period of time, cause performance reduction owing to the scattering or oxidation of noble metal(s) at high temperatures and become unable of sufficiently to oxidize combustible components; as a result, the concentration of combustible components present in the exhaust gas leaving the catalyst increases as compared to that when the catalyst is fresh.

The control for automobile exhaust gas is becoming stricter year by year owing to the increased worldwide recognition for environmental protection in recent years. For example, in California LEVs (low emission vehicles) and ULEVs (ultra low emission vehicles) must light, by law, a malfunction indicator lamp (MIL) when, during their operation, the amount of hydrocarbons discharged from the engines becomes 1.5 times the maximum hydrocarbon amount set for a new vehicle operating according to the Federal Test Procedure (FTP).

Therefore, it has been necessary to develop a method capable of detecting the performance reduction of an exhaust gas purification catalyst, particularly a method capable of detecting, at a high sensitivity, the performance reduction of an exhaust gas purification catalyst, having a high correlation with the amount of hydrocarbons discharged; and various studies have been made on the method for detection of the performance reduction of catalyst.

For example, Japanese Utility Model Application Kokai (Laid-Open) No. 62-61919 discloses a method for detection of the performance reduction of a catalyst by providing a temperature sensor both upstream and downstream of the catalyst and comparing the temperatures of exhaust gases upstream and downstream of the catalyst. This method utilizes a phenomenon that, when the catalyst shows performance reduction, the temperature of exhaust gas downstream of the catalyst decreases because the oxidation reaction of combustible components catalyzed by the catalyst is an exothermic reaction.

Japanese Utility Model Application Kokai (Laid-Open) No. 63-83415 discloses a method for detection of the performance reduction of a catalyst by providing an oxygen sensor downstream of the catalyst and analyzing the signal wave form given by the sensor. This method utilizes a phenomenon that the performance reduction of catalyst tends to reduce the oxygen adsorbability of the catalyst.

In the method for detection of the heat amount generated by the catalytic reaction, however, the difference in exhaust gas temperature between location upstream and downstream of the catalyst, brought about by the exothermic reaction can be detected only after the automobile provided with the catalyst has been operated for several minutes at a constant speed of 40–60 km/h to stabilize the exhaust gas system thermally, because the catalyst has a large heat capacity. Moreover, in the method, in order to detect the performance reduction of catalyst at a higher accuracy, longer-time operation at the above constant speed is necessary.

The operation under the above conditions is practically impossible in actual running where acceleration and deceleration are repeated, and the accurate detection of the performance reduction of catalyst by the above method is almost impossible.

In the method for detection of the oxygen adsorbability of catalyst, there are cases when the catalyst shows no reduction in oxygen adsorbability; therefore, the method has a problem in accuracy.

OBJECT AND SUMMARY OF THE INVENTION

The present invention has been made in view of the above situation. The object of the present invention is to provide a method for detection of the performance reduction of an exhaust gas purification catalyst, which can detect the performance reduction of the catalyst accurately without conducting constant-speed vehicle running for a long time.

According to the present invention, there is provided a method for detection of the performance reduction of an exhaust gas purification catalyst, which comprises; providing an exhaust gas purification catalyst used for reducing the concentration of combustible components, or the concentrations of combustible component and nitrogen oxides all present in an exhaust gas, and detecting a decrease in the heat amount $E_g$ which is generated from a unit volume of the exhaust gas in a unit time by the reaction of the exhaust gas catalyzed by the catalyst.

According to the present invention, there is further provided a method for detection of the performance reduction of an exhaust gas purification catalyst, which comprises; providing an exhaust gas purification catalyst used for reducing the concentration of combustible components, or the concentration of combustible component and nitrogen oxides all present in an exhaust gas, and detecting a decrease in the cumulative heat amount which is generated from an exhaust gas in a predetermined temperature range taken by the catalyst during its temperature increase, said cumulative heat amount being obtained by cumulating each average heat amount $E_g$ which is generated from a unit volume of the exhaust gas in a unit time by the reaction of the exhaust gas catalyzed by the catalyst, in each of the temperature zones formed by division of the predetermined temperature range.

In the latter method, it is preferable that the lower limit of the predetermined temperature range is 100°–250° C. and that the upper limit is 200°–400° C.

In each of the above two methods, the heat amount $E_g$ may be calculated from the following formula:

$$E_{out} = E_{in} + E_g - E_c - E_r$$

wherein $E_{in}$ is the heat amount possessed by an exhaust gas entering the catalyst per unit time; $E_{out}$ is the heat amount possessed by an exhaust gas leaving the catalyst per unit time; $E_r$ is the heat amount released from the catalyst per unit time; and $E_o$ is the heat amount required to change the temperature of the catalyst.

According to the present invention, there is furthermore provided a method for detection of the performance reduction of an exhaust gas system which comprises; providing the exhaust gas system comprising at least one exhaust gas purification catalyst used for reducing the concentration of combustible components or, the concentrations of combustible components and nitrogen oxides present in an exhaust gas, and detecting a decrease in the heat amount $E_g$ which is generated from a unit volume of the exhaust gas in a unit time by the reaction of the exhaust gas catalyzed by the most upstream exhaust gas purification catalyst of the system.

According to the present invention, there is still further provided a method for detection of the performance reduction of an exhaust gas system which comprises; providing the exhaust gas system comprising at least one exhaust gas purification catalyst used for reducing the concentration of combustible components or, the concentrations of combustible components and nitrogen oxides all present in an exhaust gas, and detecting a decrease in the cumulative heat amount which is generated from an exhaust gas in a predetermined temperature range taken by the most upstream exhaust gas purification catalyst of the system during its temperature increase, said cumulative heat amount being obtained by cumulating each average heat amount $E_g$ which is generated from a unit volume of the exhaust gas in a unit time by the reaction of the exhaust gas catalyzed by the most upstream exhaust gas purification catalyst of the system, in each of the temperature zones formed by division of the predetermined temperature range.

DETAILED DESCRIPTION OF THE INVENTION

In the present invention, the performance reduction of an exhaust gas purification catalyst can be detected by detecting a decrease in the heat amount $E_g$ generated from a unit volume of an exhaust gas in a unit time by the reaction of the exhaust gas catalyzed by the catalyst. Since the oxidation reaction of the combustible components present in an exhaust gas, catalyzed by an exhaust gas purification catalyst is an exothermic reaction, the above heat amount $E_g$ generated decreases when the catalyst shows a reduction in performance because the above reaction does not take place efficiently. Hence, by detecting the decrease in generated heat amount $E_g$, the performance reduction of an exhaust gas purification catalyst can be detected.

Figure 1:
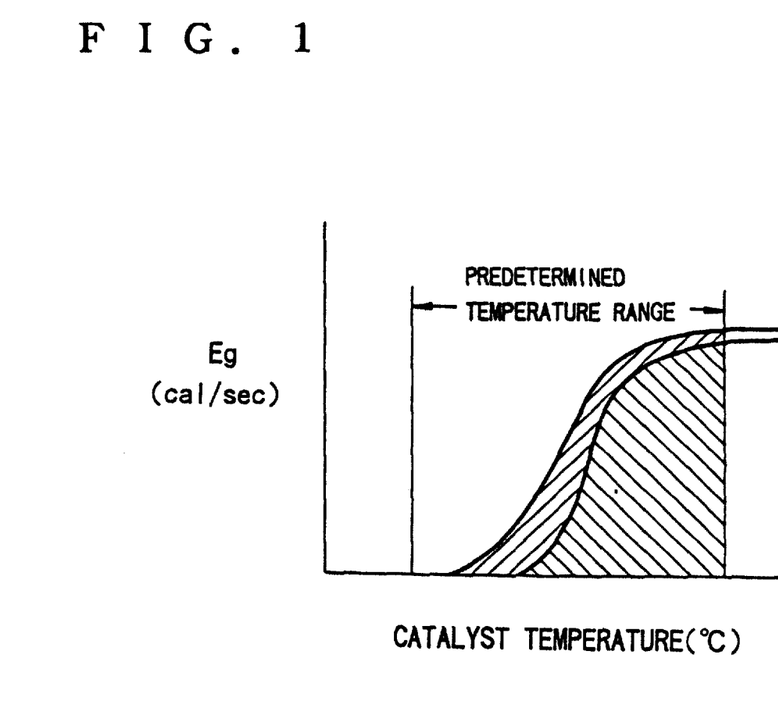
FIG. 1 is a graph showing a decrease in generated heat amount $E_g$, caused by the performance reduction of an exhaust gas purification catalyst.

Decrease in generated heat amount $E_g$, caused by the performance reduction of catalyst is shown in FIG. 1. In FIG. 1, the upper curve is for a fresh catalyst and the lower curve is for a used catalyst having a reduced performance. The ordinate and the abscissa each have a larger value as the former proceeds toward the right and the latter proceeds upward. As is clear from FIG. 1, the decrease in generated heat amount $E_g$, caused by the performance reduction of catalyst is larger when the catalyst temperature is lower. Therefore, the performance reduction of catalyst can be detected more accurately by dividing, into appropriate temperature zones, a predetermined temperature range taken by an exhaust gas purification catalyst during the catalyst temperature increase after engine start, measuring a heat amount $E_g$ generated from a unit volume of an exhaust gas in a unit time by the reaction of the exhaust gas catalyzed by the catalyst, in each temperature zone, cumulating the heat amounts $E_g$, and calculating a reduction in the cumulative heat amount obtained.

It is preferable that the lower limit of the above predetermined temperature range is 100°–250° C., preferably 150°–250° C., more preferably 150°–200° C. and that the upper limit is 200°–400° C., preferably 250°–400° C., more preferably 250°–350° C. The reasons are as follows. When the catalyst temperature is lower than 200° C., the catalyst is not activated sufficiently and the accurate detection of the performance reduction of catalyst is impossible. When the catalyst temperature is higher than 300° C., there is no big difference in generated heat amount $E_g$ between catalyst of reduced performance and fresh catalyst. Further, the hydrocarbon concentration in exhaust gas is high soon after engine start, that is, when the catalyst temperature is in the above range; therefore, the catalyst efficiency in this temperature range is most important.

In detecting the performance reduction of a catalyst specifically, there are examined, in advance, the generated heat amount $E_g$ corresponding to the allowable upper limit of hydrocarbon concentration in exhaust gas leaving the catalyst or the cumulative value of the $E_g$ in predetermined catalyst temperature range; the current level of $E_g$ or cumulative value thereof in said temperature range is measured; and, when the level reaches the above value examined in advance, the catalyst is judged to have a reduction in performance.

In the present method for detection of the performance reduction of catalyst, the generated heat amount $E_g$ is determined as follows, for example.

Figure 2:
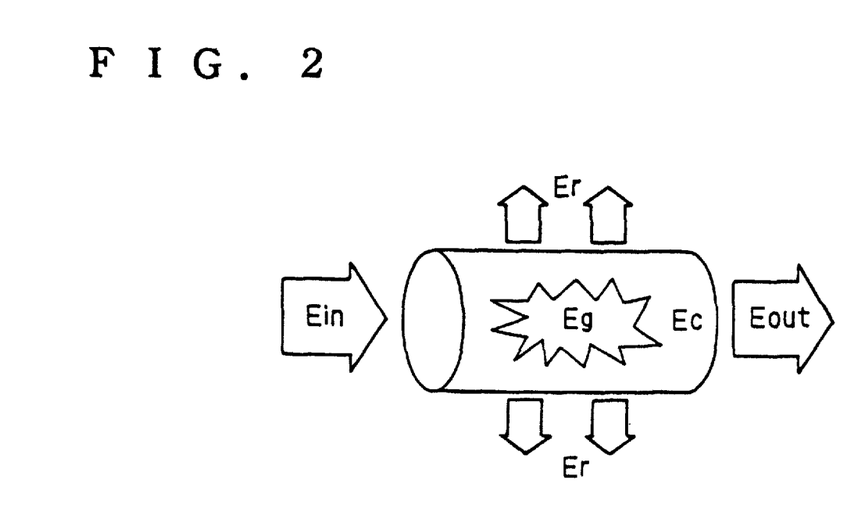
FIG. 2 is a drawing showing the heat balance seen in an exhaust gas purification catalyst.

FIG. 2 is a schematic drawing showing the heat balance of a catalyst. In FIG. 2, $E_{in}$ is the heat amount possessed by an exhaust gas entering the catalyst per unit time; $E_{out}$ is the heat amount possessed by an exhaust gas leaving the catalyst per unit time; $E_r$ is the heat amount released from the catalyst per unit time; and $E_c$ is the heat amount required to change the temperature of the catalyst. Between $E_{in}$, $E_g$, $E_c$, $E_r$ and $E_{out}$, the following relation [formula (1)] holds:

$$E_{out}=E_{in}+E_g-E_c-E_r \qquad (1)$$

$E_{in}$ and $E_{out}$ can be calculated from the following formulas (2) and (3), respectively, by measuring the temperature and volume of exhaust gas:

$$E_{in}(\text{cal/sec})=Q \cdot Hs \cdot T1 \qquad (2)$$

$$E_{out}(\text{cal/sec})=Q \cdot Hs \cdot T2 \qquad (3)$$

wherein Hs is the specific heat of exhaust gas; Q is the volume of exhaust gas per unit time; T1 is the temperature of an exhaust gas entering the catalyst; and T2 is the temperature of an exhaust gas leaving the catalyst.

$E_r$ and $E_c$, which are both irrelevant to the performance reduction of catalyst, can be determined beforehand.

$E_r$ can be calculated from the temperature of catalyst by determining the relation between the temperature of catalyst and the heat amount released from the catalyst. $E_r$ can be calculated specifically as follows.

When an engine or the like is operated in a steady state, the temperature of catalyst is constant and the heat amount possessed by exhaust gas is not consumed for the temperature increase of catalyst. Therefore, $E_c=0$ in the formula (1) ($E_{out}=E_{in}+E_g-E_c-E_r$). Incidentally, "steady state" refers to a state in which the temperature of exhaust gas system is stabilized and the temperature of catalyst is constant.

When an engine or the like is operated in a steady state with no noble metal supported on catalyst, $E_g$ (generated heat amount)=0. Accordingly, the formula (1) can be rewritten as follows.

$$E_r = E_{in} - E_{out} \qquad (4)$$

The formula (4) can be rewritten as follows, using the formulas (2) and (3).

$$E(cal/sec) = Q \cdot Hs \cdot (T1-T2) \qquad (5)$$

Thus, $E_r$ can be calculated from the formula (5), by measuring T1, T2 and Q when an engine or the like is operated in a steady state with no noble metal supported on catalyst. By determining a plurality of $E_r$S in various steady states of different catalyst temperatures, a relation between the temperature of catalyst and $E_r$ can be obtained.

$E_c$ can be calculated specifically as follows.

When an engine is operated with no noble metal supported on catalyst, only the generated heat amount $E_g$ can be regarded as 0 (zero) during the period after engine start but before steady state. Hence, the formula (1) can be rewritten as follows.

$$E_c = E_{in} - E_{out} - E_r \qquad (6)$$

The formula (6) can be rewritten as follows.

$$\Sigma E_c = \Sigma(E_{in} - E_{out} - E_r) \qquad (7)$$

By measuring T1, T2, Q and the temperature of catalyst per each unit time during the period after engine start but before steady state and by using $E_r$ determined from the relation between the temperature of catalyst and $E_r$, $\Sigma E_c$ in certain temperature range can be calculated from the formula (7). By preparing a graph showing a relation between the temperature of catalyst and $\Sigma E_c$ and determining the inclination thereof, $E_c$ can be determined.

Thus, $E_{in}$, $E_{out}$, $E_r$ and $E_c$ can be calculated from various measurement values; consequently, $E_g$ can be calculated from them.

The cumulative value of $E_g$ in predetermined catalyst temperature range can be obtained in accordance with, for example, the procedure shown in Table 1.

First, there are measured T1, T2, Q and the temperature of catalyst during a predetermined temperature range taken by catalyst during its temperature increase after engine start, per each unit time. Then, using the T1, T2 and Q and the formulas (3) and (4), $E_{in}$ and $E_{out}$ per each unit time are calculated. In Table 1, unit time is 1 (one) second.

Next, using the $E_r$ and $E_c$ obtained beforehand, the above-obtained $E_{in}$ and $E_{out}$ and the formula (1), $E_g$ (cal/sec) per each unit time is calculated.

Using the measured Q, $E_g$ per each unit volume of exhaust gas is calculated per each unit time. In Table 1, unit volume is 1 (one) liter. Therefore, the $E_g$ at this stage has a unit of cal/sec·l.

Next, the predetermined catalyst temperature range mentioned above is appropriately divided into a plurality of temperature zones each having a span of 10° C., 20° C. or the like; and there is calculated an average heat amount $E_g$ (cal/sec·l) generated per each unit time per each unit volume in each temperature zone.

Lastly, there is calculated the total of each average heat amount $E_g$ (cal/sec·l) generated in each temperature zone, whereby the cumulative value (cal/sec·l) of generated heat amounts $E_g$ is calculated.

Figure 3:
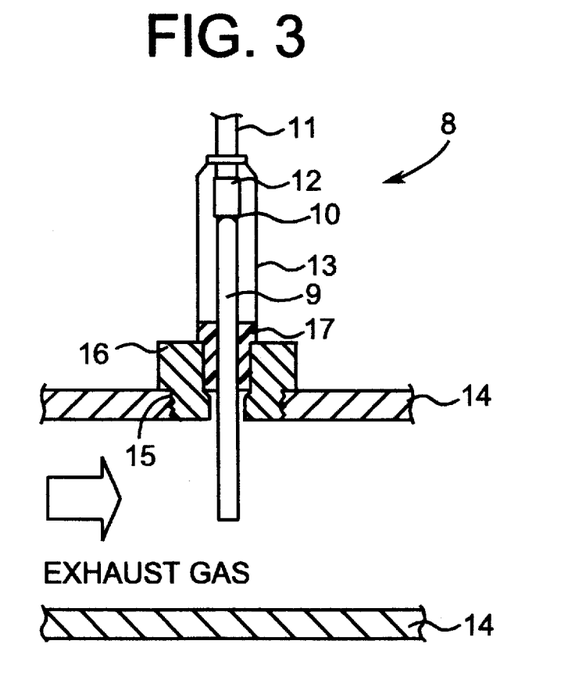
FIG. 3 is a sectional drawing showing an example of the temperature sensor used in the method of the present invention.

In the present invention, measurement of temperature is conducted by the use of a temperature sensor, a thermocouple or the like. Temperature measurement by a temperature sensor is preferred. As the temperature sensor, there is used, for example, one shown in FIG. 3. In FIG. 3, the temperature sensor 3 is covered with a ceramic material and comprises a resistor 9 containing a metal having a positive temperature coefficient of resistance, a potentiometric resistance 10 connected to one end of the resistor 9, a connector 12 connecting the potentiometric resistance 10 and a line 11, and a casing 13 accommodating one end of the resistor 9, the potentiometric resistance 10, the connector 12 and one end of the line 11. This temperature sensor 8 measures the temperature of exhaust gas by utilizing a fact that the resistance of the resistor 9 changes in accordance with the change of the temperature, and is used by inserting one end of the resistor 9 projecting from the casing 13, into an exhaust pipe 14 through a hole 15 made in the wall of the exhaust pipe 14. The fixation of the resistor 9 to the hole 15 is conducted via a housing 16 having a portion engaged with the hole 15. A buffer material 17 is used between the housing 16 and the resistor 9. One end of the resistor 9 positioned inside the exhaust pipe may be covered with a protective material.

Measurement of flow amount of exhaust gas can be determined from the negative pressure of intake gas and the rpm of engine by calculation or experiment, or from the amount of fuel injected and A/F. Alternatively, it may be determined from the sum of (a) the amount of air introduced, obtained by an MAF (mass air flow) sensor and (2) the amount of fuel converted to the amount of combustion gas, or only from the amount of air introduced, obtained by an MAF sensor because the amount of air introduced and the amount of fuel have a nearly constant ratio.

The present invention method enables rapid and easy detection of the performance reduction of an exhaust gas purification catalyst without conducting constant-speed vehicle running for a long time. Further, since there is a high correlation between (1) generated heat amount $E_g$ or its cumulative value in predetermined catalyst temperature range and (2) hydrocarbon concentration in exhaust gas, the present invention method enables accurate detection of the performance reduction of catalyst and, moreover, can examine the conformity of a vehicle to the above-mentioned hydrocarbon control set by California for FTP running.

An exhaust gas system is ordinarily constituted by connecting a plurality of exhaust gas purification catalysts to an internal combustion engine or the like. When the performance reduction of such an exhaust gas system is required to be detected, detection of the performance reduction of the most upstream exhaust gas purification catalyst is sufficient when the internal combustion engine side of the exhaust gas system is regarded as the upstream side thereof. This is because (1) hydrocarbons are generated only at the initial period of engine start, (2) the plurality of catalysts reach their activation temperatures in the order of the most up-stream catalyst, the next upstream catalyst, . . . . . . . . . and (3) most of the hydrocarbons are treated by the most upstream catalyst.

The present invention is hereinafter described by way of Example. However, the present invention is not restricted to the Example.

Using the above-mentioned method of the present invention, the performance reduction of exhaust gas purification catalyst was detected and the hydrocarbon concentration in exhaust gas leaving the catalyst was examined.

Figure 4:
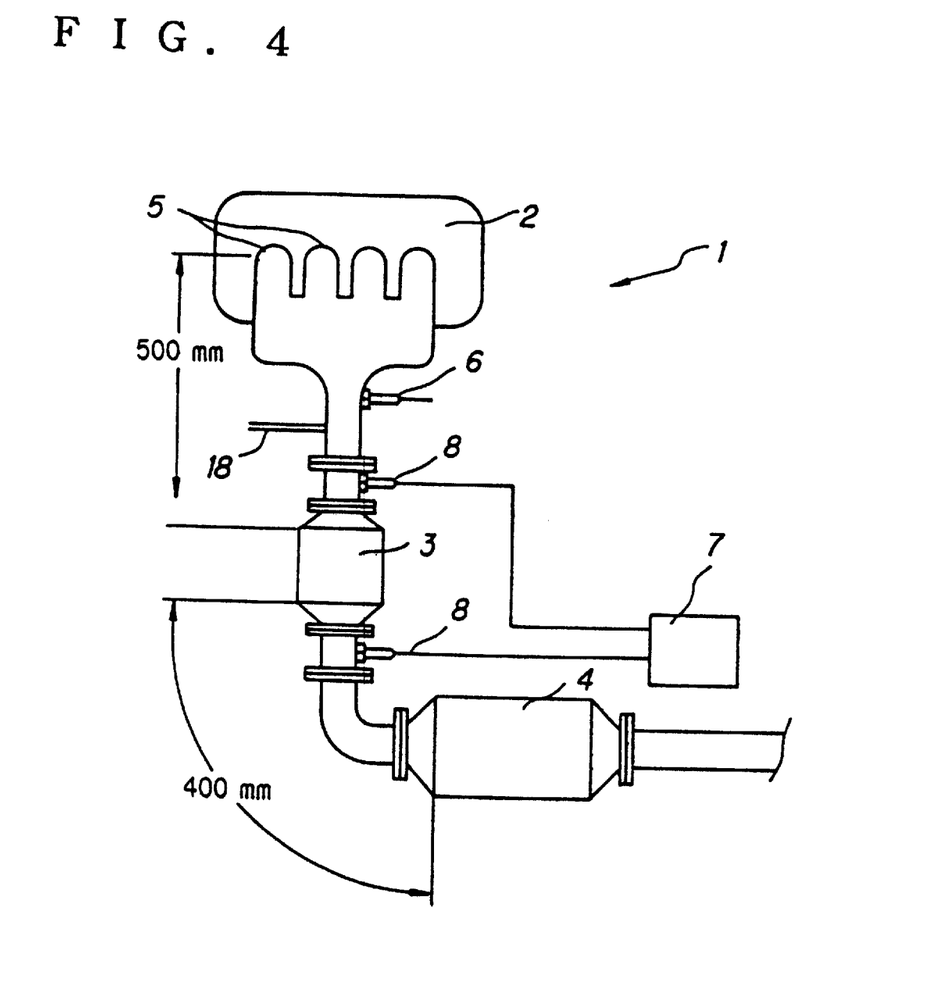
FIG. 4 is a drawing showing an exhaust gas system of an automobile engine.

In FIG. 4 is shown the exhaust gas system used in the present Example. The exhaust gas system 1 of FIG. 4 comprises a 2.0-liter in-line four-cylinder engine 2, a 600cc light-off catalyst 3 connected to the engine 2 and a 1,700-cc main catalyst 4 connected to the catalyst 3. The light-off catalyst 3 is provided at a position 500 mm from the discharge port 5 of the engine 2; and the main catalyst 4 is provided at a position 400 mm from the lower end of the light-off catalyst 3. A temperature sensor 8 is fitted both upstream and downstream of the light-off catalyst 3. Further upstream of the light-off catalyst 3 is fitted an $O_2$ sensor 6 for A/F control. The outputs of the temperature sensors 8 are sent to a device 7 for measurement, control and calculation.

The exhaust gas generated in the engine 2 passes through the light-off catalyst 3 and is discharged. The device 7 for measurement, control and calculation reads the signals sent from the temperature sensors 8, calculates the cumulative value of generated heat amount $E_g$ and, depending upon the level of the value, issues a signal for lighting of MIL or the like.

$E_r$ and $E_c$ were determined prior to the detection of the performance reduction of catalyst.

[Calculation of $E_r$]

An exhaust gas system shown in FIG. 4 was mounted on an automobile with no noble metal supported on the catalyst of the system. The automobile was operated at speeds of 20 km/h, 40 km/h, 60 km/h and 80 km/h for 30 minutes each. In the respective steady-state operations of different speeds, there were measured the temperatures (T1 and T2) of exhaust gases upstream and downstream of the catalyst, and the flow amount (Q) (l/sec) of exhaust gas.

Figure 5:
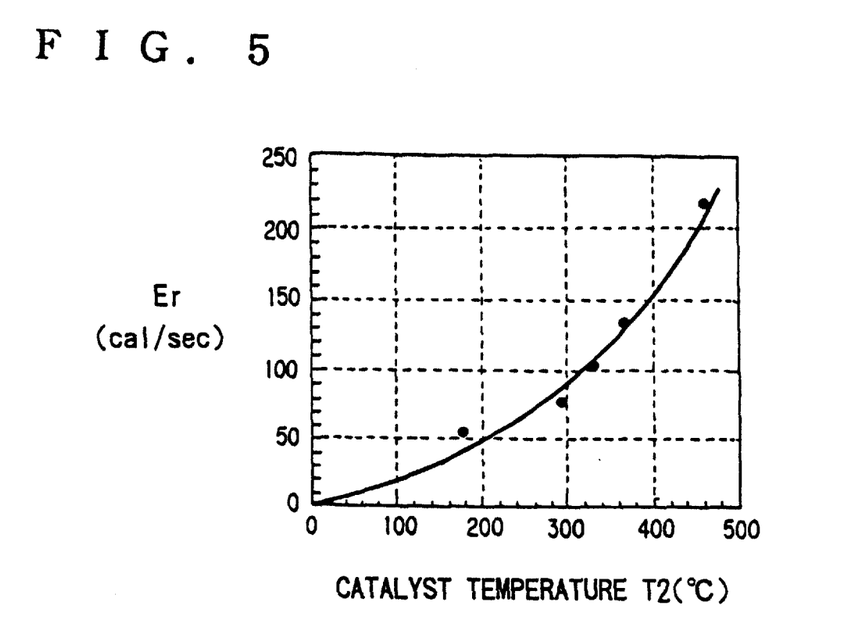
FIG. 5 is a graph showing a relation between the heat amount $E_r$ released from an exhaust gas purification catalyst per unit time and the temperature of the catalyst.

Using the above-obtained T1, T2 and Q and the formula (5), $E_r$s at different speeds were calculated. Incidentally, there was used, as Hs, the specific heat of air, i.e. 0.306 cal/l·°C. In FIG. 5 is shown a relation between $E_r$ obtained and corresponding catalyst temperature. Incidentally, T2 was used as the catalyst temperature.

[Calculation of $E_c$]

An exhaust gas system shown in FIG. 4 was mounted on an automobile with no noble metal supported on the catalyst of the system. The automobile was operated in the FTP running mode. T1, T2 and Q were measured every second after the start of engine.

Figure 6:
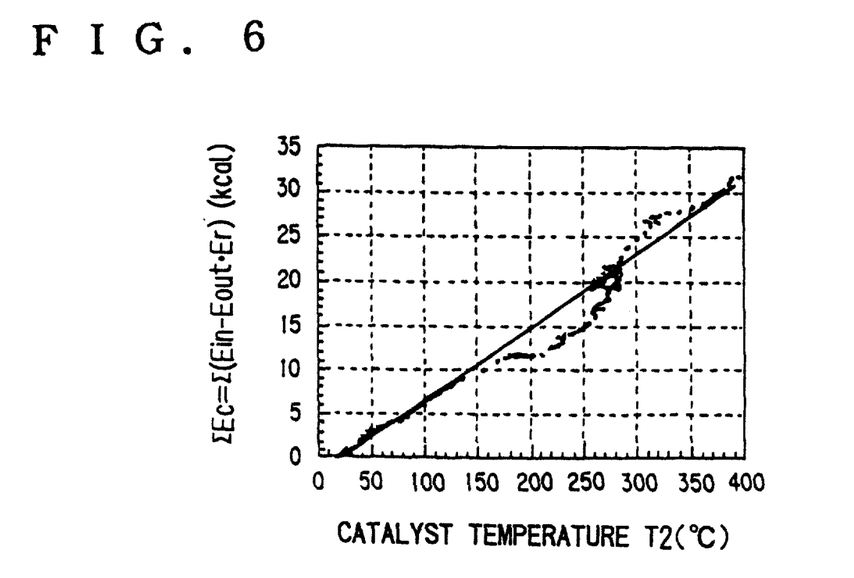
FIG. 6 is a graph showing a relation between the temperature of an exhaust gas purification catalyst and the cumulative value $\Sigma E_c$ of the heat capacity of the catalyst in a predetermined catalyst temperature range.

Using the above-obtained T1s, T2s and Qs, the $E_r$s obtained from FIG. 4 with T2s regarded as catalyst temperatures, and the formula (7), there was calculated $\Sigma E_c$ in the catalyst temperature range from room temperature to 400° C. In FIG. 6 is shown a relation between catalyst temperature and $\Sigma E_c$. From the average of the inclinations of the FIG. 6 graph from 25° C. to 300° C., $E_c$ was calculated as 83.6 cal/° C.

[Measurement of hydrocarbon concentration in exhaust gas]

Four identical exhaust gas systems A, B, C and D as shown in FIG. 4 were prepared. B, C and D were subjected to aging under the conditions shown in Table 2. In the aging, the main catalyst 4 was provided at a position 15 cm down-stream of the lower end of the light-off catalyst 3. During the aging, the temperature of exhaust gas was maintained at 750° C. upstream of the light-off catalyst 3. In Table 2, the aging temperature of the main catalyst 4 is higher than that of the light-off catalyst 3, owing to the reaction heat generated by catalysis.

TABLE 2

| Exhaust gas system | Light-off catalyst | Main catalyst |
| --- | --- | --- |
| A | Fresh | Fresh |
| B | Aging of 750° C. × 100 hours | Aging of 805° C. × 100 hours |
| C | Aging of 750° C. × 200 hours | Aging of 805° C. × 200 hours |
| D | Aging of 750° C. × 300 hours | Aging of 805° C. × 300 hours |

Each of the resulting exhaust gas systems was mounted on an automobile, and measured for the hydrocarbon amount discharged in the FTP running mode. The results are shown in Table 3.

TABLE 3

| Exhaust gas system | Hydrocarbon amount discharged (g/mile) |
| --- | --- |
| A | 0.058 |
| B | 0.063 |
| C | 0.070 |
| D | 0.098 |

[Detection of performance reduction of exhaust gas purification catalyst]

Each of the exhaust gas systems shown in Table 2 was mounted on an automobile and measured for the T1, T2 and Q appearing in the FTP running mode, every second. Since many LEVs have a secondary air injection device for higher catalyst activity, there was provided, also in the present Example, an inlet 18 for secondary air injection upstream of the light-off catalyst 3, and air was injected therefrom in an amount of 120 cc/min for 100 seconds from the start of engine to simulate the operating conditions to those of LEV.

Using each T1, T2, Q obtained above and the formulas (2) and (3), $E_{in}$ and $E_{out}$ per every second were calculated for each exhaust gas system. $E_{in}$ and $E_{out}$ were calculated in the catalyst temperature range from 100° C. to 320° C. (T2 was regarded as the catalyst temperature). Using these values obtained and the formula (1), there was calculated the heat amount $E_g$ generated per every second per one liter of exhaust gas after the start of engine.

Next, the above temperature range from 100° C. to 320° C. was divided into temperature zones each of 20° C. span, for example, 100°–120° C., 120°–140° C., etc.; and there was calculated, for each temperature zone, an average of the heat amounts $E_g$ generated per one liter of exhaust gas per every second.

The average of the heat amounts $E_g$ generated in each temperature zone was summed up to calculate, for each exhaust gas system, the cumulative value of the average heat amounts $E_g$ generated in the individual temperature zones of the temperature range from 100° C. to 320° C.

Figure 7:
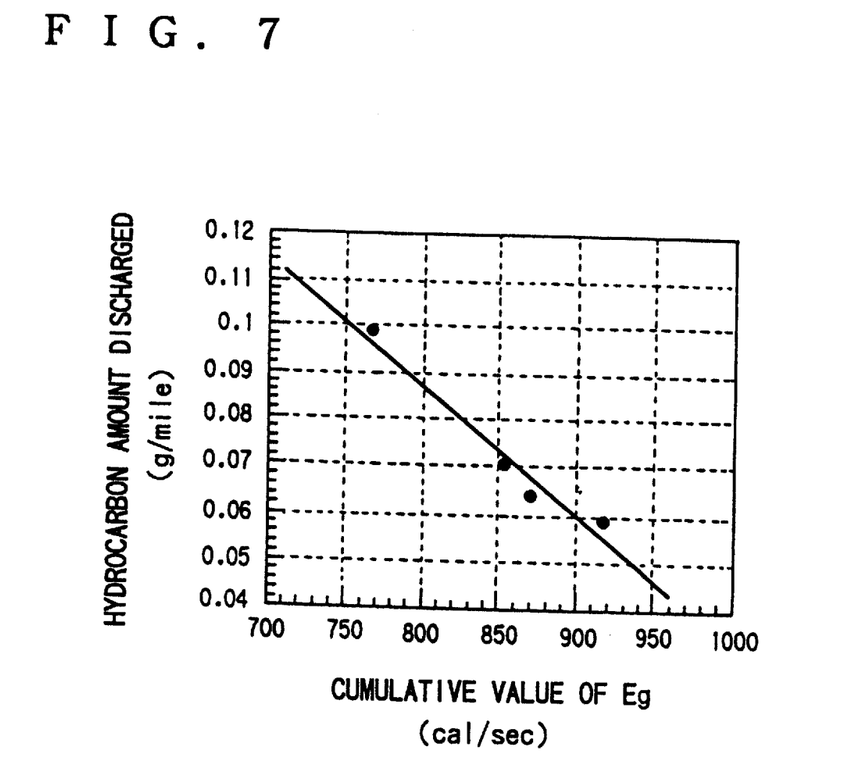
FIG. 7 is a graph showing a relation between (1) the cumulative value of generated heat amounts $E_g$ and (2) the hydrocarbon amount discharged.

In FIG. 7 is shown a relation between the cumulative value of generated heat amounts $E_g$ and the amount of hydrocarbons discharged. In FIG. 7, the coefficient of correlation between the cumulative value of generated heat amounts $E_g$ and the amount of hydrocarbons discharged is 0.956 and the correlation between them is high.

The hydrocarbon limit for new ULEV in the FTP running mode is 0.04 g/mile. The cumulative value of generated heat amounts $E_g$ when the hydrocarbon amount discharged has reached 1.5 times the above hydrocarbon limit, i.e. 0.06 g/mile, can be obtained from FIG. 7. Thus, a malfunction indicator lamp (MIL) can be lighted when the cumulative value of $E_g$s of a vehicle has reached the value obtained above from FIG. 7.

In the present invention, the performance reduction of an exhaust gas purification catalyst can be detected from a decrease in the heat amount $E_g$ generated from an exhaust gas by the reaction of the exhaust gas catalyzed by the catalyst, or from a decrease in the cumulative value of the heat amounts $E_g$ generated in the individual temperature zones of a predetermined catalyst temperature range. Therefore, the present method enables rapid, easy and accurate detection of the performance reduction of exhaust gas purification catalyst without conducting a constant-speed vehicle operation of long time. Further, the present method for detection of the performance reduction of an exhaust gas purification catalyst can examine the conformity of a vehicle to the above-mentioned hydrocarbon control set by California for FTP running.

What is claimed is:

1. A method for detection of the performance reduction of an exhaust gas purification catalyst, comprising;

providing an exhaust gas purification catalyst used for reducing (a) the concentration of combustible components or (b) the concentrations of combustible component and nitrogen oxides all present in an exhaust gas, and beginning at an initial stage of engine operation soon after an engine starts detecting a decrease in catalyst efficiency which is measured by the heat amount $E_g$ generated from a unit volume of the exhaust gas in a unit time by the reaction of the exhaust gas catalyzed by said catalyst.

2. A method for detection of the performance reduction of an exhaust gas purification catalyst, comprising;

providing an exhaust gas purification catalyst used for reducing (a) the concentration of combustible components or (b) the concentrations of combustible component and nitrogen oxides all present in the exhaust gas, and detecting a decrease in catalyst efficiency which is measured by the cumulative heat amount generated from an exhaust gas during a temperature increase of the catalyst in a predetermined temperature range, said cumulative heat amount being obtained by cumulating each average heat amount $E_g$ generated from a unit volume of the exhaust gas in a unit time by oxidation of combustible components by the catalyst, in each of the temperature zones formed by division of the predetermined temperature range, said detecting beginning at an initial stage of engine operation soon after an engine starts.

3. A detection method according to claim 2, wherein the lower limit of the predetermined temperature range is 100°–250° C. and the upper limit is 200°–400° C.

4. A detection method according to claim 1, wherein Eg is calculated from the following formula:

$$E_{out}=E_{in}+E_g-E_c-E_r$$

wherein $E_{in}$ is the heat amount possessed by an exhaust gas entering the catalyst per unit time; $E_{out}$ is the heat amount possessed by an exhaust gas leaving the catalyst per unit time; $E_r$ is the heat amount released from the catalyst per unit time; and $E_c$ is the heat amount required to change the temperature of the catalyst.

5. A detection method according to claim 2, wherein Eg is calculated from the following formula:

$$E_{out}=E_{in}+E_g-E_c-E_r$$

wherein $E_{in}$ is the heat amount possessed by an exhaust gas entering the catalyst per unit time; $E_{out}$ is the heat amount possessed by an exhaust gas leaving the catalyst per unit time; $E_r$ is the heat amount released from the catalyst per unit time; and $E_c$ is the heat amount required to change the temperature of the catalyst.

6. A method for detection of the performance reduction of an exhaust gas system which comprises;

providing an exhaust gas system comprising at least one exhaust gas purification catalyst used for reducing (a) the concentration of combustible components or (b) the concentrations of combustible components and nitrogen oxides all present in an exhaust gas, and beginning at an initial stage of engine operation soon after an engine starts detecting a decrease in catalyst efficiency which is measured by the heat amount $E_g$ generated from a unit volume of the exhaust gas in a unit time by the reaction of the exhaust gas catalyzed by the most upstream exhaust gas purification catalyst of the system.

7. A method for detection of the performance reduction of an exhaust gas system comprising;

providing an exhaust gas system comprising at least one exhaust gas purification catalyst used for reducing (a)

the concentration of combustible components or (b) the concentrations of combustible components and nitrogen oxides all present in an exhaust gas, and detecting a decrease in catalyst efficiency which is measured by the cumulative heat amount generated from an exhaust gas during a temperature increase of the most upstream catalyst in a predetermined temperature range, said cumulative heat amount being obtained by cumulating each average heat amount $E_g$ generated from a unit volume of the exhaust gas in a unit time by the reaction of the exhaust gas catalyzed by the most upstream exhaust gas purification catalyst of the system, in each of the temperature zones formed by division of the predetermined temperature range, said detecting beginning at an initial stage of engine operation soon after an engine starts.

8. A detection method according to claim 6, wherein the lower limit of the predetermined temperature range is 100°–250° C. and the upper limit is 200°–400° C.

9. A detection method according to claim 7, wherein the lower limit of the predetermined temperature range is 100°–250° C. and the upper limit is 200°–400° C.

10. A detection method according to claim 6, wherein Eg is calculated from the following formula:

$$E_{out} = E_{in} + E_g - E_c - E_r$$

wherein $E_{in}$ is the heat amount possessed by an exhaust gas entering the catalyst per unit time; $E_{out}$ is the heat amount possessed by an exhaust gas leaving the catalyst per unit time; $E_r$ is the heat amount released from the catalyst per unit time; and $E_c$ is the heat amount required to change the temperature of the catalyst.

11. A detection method according to claim 7, wherein Eg is calculated from the following formula:

$$E_{out} = E_{in} + E_g - E_c - E_r$$

wherein $E_{in}$ is the heat amount possessed by an exhaust gas entering the catalyst per unit time; $E_{out}$ is the heat amount possessed by an exhaust gas leaving the catalyst per unit time; $E_r$ is the heat amount released from the catalyst per unit time; and $E_c$ is the heat amount required to change the temperature of the catalyst.

* * * * *